US010391161B2

(12) United States Patent
Kuo et al.

(10) Patent No.: US 10,391,161 B2
(45) Date of Patent: Aug. 27, 2019

(54) FSBM RECOMBINANT PROTEIN

(71) Applicant: I-SHOU UNIVERSITY, Kaohsiung (TW)

(72) Inventors: Chih-Feng Kuo, Kaohsiung (TW); Ni-Na Tsao, Kaohsiung (TW)

(73) Assignee: I-SHOU UNIVERSITY, Kaohsiung (TW)

( * ) Notice: Subject to any disclaimer, the term of this patent is extended or adjusted under 35 U.S.C. 154(b) by 0 days.

(21) Appl. No.: 15/461,120

(22) Filed: Mar. 16, 2017

(65) Prior Publication Data

US 2018/0169209 A1 Jun. 21, 2018

(30) Foreign Application Priority Data

Dec. 19, 2016 (TW) ............................ 105142098 A

(51) Int. Cl.
*A61K 39/09* (2006.01)
*A61K 39/00* (2006.01)

(52) U.S. Cl.
CPC ........ *A61K 39/092* (2013.01); *A61K 2039/54* (2013.01); *A61K 2039/545* (2013.01)

(58) Field of Classification Search
None
See application file for complete search history.

(56) References Cited

U.S. PATENT DOCUMENTS 7,160,547 B2 * 1/2007 Dale .................. C07K 16/1275 424/184.1
7,424,370 B2 * 9/2008 Sachdeva ........... G01N 33/6803 702/19
7,709,009 B2 * 5/2010 Grandi ................. A61K 39/092 424/184.1
7,838,010 B2 * 11/2010 Bensi ................... C07K 14/315 424/184.1
8,128,936 B2 * 3/2012 Grandi ................. A61K 39/092 424/184.1
2002/0086023 A1 * 7/2002 Dale .................. C07K 16/1275 424/178.1
2003/0157122 A1 * 8/2003 Dale .................. C07K 16/1275 424/190.1
2006/0165716 A1 * 7/2006 Telford .............. A61K 39/0208 424/190.1
2009/0318420 A1 * 12/2009 Horvath ............... C07D 223/16 514/212.07
2010/0150943 A1 * 6/2010 Grandi ................. A61K 39/092 424/165.1
2018/0169209 A1 * 6/2018 Kuo ..................... A61K 39/092
2019/0094220 A1 * 3/2019 Kuo ................. G01N 33/56944

FOREIGN PATENT DOCUMENTS

WO WO-2005032582 A2 * 4/2005 ........... A61K 39/092

OTHER PUBLICATIONS

Kuo et al, Eur. J. Immunol. 2016. 46 (Suppl. 1): 1-1274, see p. 1220 Abstract #1323 (Year: 2016).*
Dale et al, Nfection and Immunity, Apr. 2002, p. 2166-2170 vol. 70, No. 4 (Year: 2002).*
Kuo et al, PLoS One 12(3): e0174464.2017. published Mar. 29, 2017 (Year: 2017).*
Sumby et al. PLoS Pathogens | www.plospathogens.org 0041 Jan. 2006 | vol. 2 | Issue 1 | e5 (Year: 2006).*
Hung et al, Med Microbiol Immunol (2012) 201:357-369 (Year: 2012).*
Steer et al, Curr. Opin. Infect Dis, 2009, 22:544-552. (Year: 2009).*
Kuo et al, PLoS One, 2017, 12/3:e1074464, 20 pages. published Mar. 29, 2017. (Year: 2017).*
Sunby et al, PLoS Pathogens, Jan. 2006, 2/1:e5, 0041-0049 (Year: 2006).*
Abstracts of ICI 2016, International Congress of Immunology, European Journal of Immunology, vol. 46, Suppl. 1, Aug. 21-26, 2016, Melbourne, Australia.

* cited by examiner

*Primary Examiner* — Nita M. Minnifield
(74) *Attorney, Agent, or Firm* — WPAT, PC

(57) ABSTRACT

The invention discloses a FSBM recombinant protein for conferring protection against group C *streptococcus* infection in an animal subject, comprising: a first peptide fragment, having an amino acid sequence set forth as SEQ ID NO. 5; a second peptide fragment, having an amino acid sequence set forth as SEQ ID NO. 6; a third peptide fragment, having an amino acid sequence set forth as SEQ ID NO. 7; and a fourth peptide fragment, having an amino acid sequence set forth as SEQ ID NO. 8. The invention also discloses a method of protecting an animal subject against group C *streptococcus* infection.

5 Claims, 4 Drawing Sheets

Specification includes a Sequence Listing.

FSBM RECOMBINANT PROTEIN

CROSS REFERENCE TO RELATED APPLICATIONS

The application claims the benefit of Taiwan application serial No. 105142098, filed Dec. 19, 2016, the subject matter of which is incorporated herein by reference.

BACKGROUND OF THE INVENTION

1. Field of the Invention

The present invention generally relates to a FSBM recombinant protein, and more particularly, to a FSBM recombinant protein for conferring protection against group C *streptococcus* infection in an animal subject.

2. Description of the Related Art

*Streptococcus* is a genus of spherical Gram-positive bacteria belonging to the phylum Firmicutes. Cell division in this genus occurs along a single axis in these bacterial, thus they grow in chains or pairs; and therefore are named as *Streptococcus*.

Group B *streptococcus* and group C *streptococcus* are the main pathogens causing *streptococcus* infection in poultry and livestock. As an example, group C *streptococcus* infection may cause strangles in horses, as well as septic *streptococcus* infection in sheep and pig.

Clinically, antibiotics such as penicillin G and cephalosporin can be used to treat group C *streptococcus* infection. However, excess use of antibiotics is not only the reason of allergy in consumer of animal by-products, but also the factor contributing to emergence of drug-resistant pathogens. In light of this, it is necessary to provide a vaccine for conferring protection against group C *streptococcus* infection in an animal subject.

SUMMARY OF THE INVENTION

It is therefore the objective of this invention to provide a FSBM recombinant protein for conferring protection against group C *streptococcus* infection in an animal subject.

One embodiment of the invention discloses a FSBM recombinant protein or conferring protection against group C *streptococcus* infection in an animal subject. The FSBM recombinant protein comprises a first peptide fragment, having an amino acid sequence set forth as SEQ ID NO. 5; a second peptide fragment, having an amino acid sequence set forth as SEQ ID NO. 6; a third peptide fragment, having an amino acid sequence set forth as SEQ ID NO. 7; and a fourth peptide fragment, having an amino acid sequence set forth as SEQ ID NO. 8. Preferably, the FSBM recombinant protein has an amino acid sequence set forth as SEQ ID NO. 10.

Another embodiment of the invention discloses a method of protecting an animal subject against group C *streptococcus* infection by immunizing the animal subject with said FSBM recombinant protein to facilitate production of antibody against group C *streptococcus* in the animal subject.

In a preferred form shown, the FSBM recombinant protein is immunized the animal subject by either intramuscular injection or subcutaneous injection.

In a preferred form shown, the FSBM recombinant protein is immunized the animal subject in a dosage of 1 mg/kg of the animal subject once in 7 days.

BRIEF DESCRIPTION OF THE DRAWINGS

The present invention will become more fully understood from the detailed description given hereinafter and the accompanying drawings which are given by way of illustration only, and thus are not limitative of the present invention, and wherein.

Figure 1A:
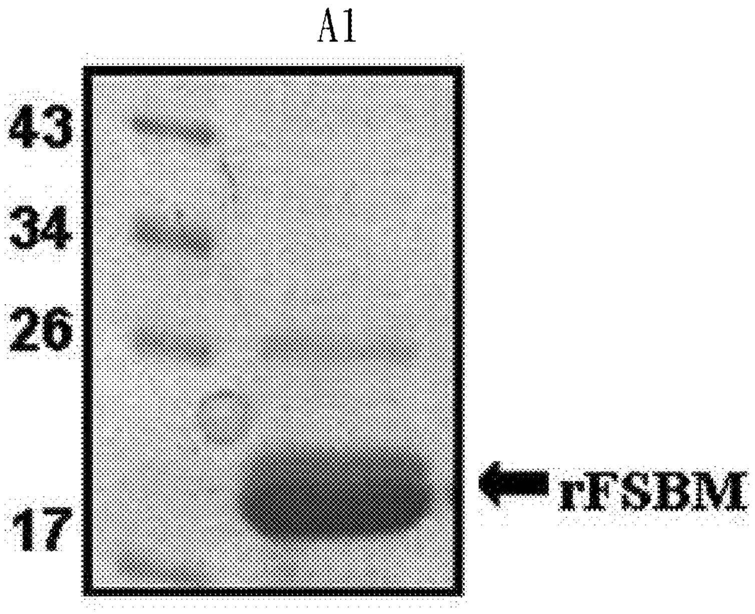
FIG. 1*a* depicts the SDS-PAGE analysis of the FSBM recombinant protein according to the present invention.

In the various figures of the drawings, the same numerals designate the same or similar parts. Furthermore, when the term "first", "second", "third", "fourth" and similar terms are used hereinafter, it should be understood that these terms refer only to the structure shown in the drawings as it would appear to a person viewing the drawings, and are utilized only to facilitate describing the invention.

DETAILED DESCRIPTION OF THE INVENTION

A FSBM recombinant protein according to the present invention comprises a first peptide fragment, a second peptide fragment, a third peptide fragment and a fourth peptide fragment. The first peptide fragment is derived from a partial fragment of the FnBR domain of Sfb1 (one of the fibronectin-binding proteins), the second peptide fragment is derived from a partial fragment of the immunogenic domain of SLS (streptolysin S), the third peptide fragment is derived from a partial fragment of the C3-binding motif of SPE B (streptococcal pyrogenic exotoxin B), and the fourth peptide fragment is derived from a partial fragment of the C-terminal conserved segment of M protein.

The FSBM recombinant protein can be expressed by *E. coli* cells. As an example, an expression plasmid for expressing the FSBM recombinant protein can be constructed and transformed into the *E. coli* cells. The FSBM recombinant protein expressed by the *E. coli* cells can be purified, and the purified FSBM recombinant protein can therefore be obtained.

Specifically, the expression plasmid comprises a first DNA fragment corresponding to the first peptide fragment, a second DNA fragment corresponding to the second peptide fragment, a third DNA fragment corresponding to the third peptide fragment and a fourth DNA fragment corresponding to the fourth peptide fragment. Moreover, the first, second, third and fourth DNA fragments preferably have the codon usage of *E. coli*, thus the *E. coli* cells can show preferable expression efficiency. In this embodiment, the first, second, third and fourth DNA fragments have nucleic acid sequences set forth as SEQ ID NOS: 1, 2, 3 and 4, respectively. In addition, the first, second, third and fourth peptide fragments expressed by the *E. coli* cells have the amino acid sequences set forth as SEQ ID NOS: 5, 6, 7 and 8, respectively.

Furthermore, a linker fragment can be added between the first and second DNA fragments, the second and third DNA fragments, and the third and fourth DNA fragments. The sequence of the linker fragment can be appreciated by a person having ordinary skill in the art; and therefore detail description is not given to avoid redundancy. In this embodiment, the expression plasmid comprises a nucleic acid sequence set forth as SEQ ID NO: 9, while the FSBM recombinant protein expressed by the *E. coli* cells has an amino acid sequence set forth as SEQ ID NO: 10.

The construction of the expression plasmid is the prior art well-known in the field; and therefore is not limited to the following statement. In this embodiment, the DNA fragment with the nucleic acid sequence set forth as SEQ ID NO: 9 is synthesized and digested by the restriction enzyme. The digested DNA fragment is then ligated to a pET-24a vector by a ligase, and the expression plasmid is obtained.

In this embodiment, after the expression plasmid is transformed into the *E. coli* BL21(DE) pLysS, the *E. coli* BL21(DE) pLysS can express the fusion protein with 6×His tag by IPTG induction. The FSBM recombinant protein can be then purified using $Ni^{2+}$ chelating chromatography.

The purified FSBM recombinant protein can be used to immunize an animal subject to induce production of an antibody against group C *streptococcus*, conferring protection against group C *streptococcus* infection in the animal subject. As an example, the FSBM recombinant protein can be immunized the animal subject in a dosage of 1 mg/kg of the animal subject once in 7 days for 3 times by either intramuscular injection (IM injection) or subcutaneous injection (SC injection).

Moreover, a pharmaceutically-acceptable adjuvant can be mixed with the purified FSBM recombinant protein to form a group C *streptococcus* vaccine. The pharmaceutically-acceptable adjuvant can improve the stability of the FSBM recombinant protein in the animal subject. Alternatively, the pharmaceutically-acceptable adjuvant can enhance immune responses of the FSBM recombinant protein; and therefore the FSBM recombinant protein have a preferable effect on inducing the production of the antibody against group C *streptococcus*. Specifically, the pharmaceutically-acceptable adjuvant can be an oil-based adjuvant or an oil-in-water adjuvant. As an example, the oil-based adjuvant can be complete Freund's adjuvant (CFA) or incomplete Freund's adjuvant (IFA), and the oil-in-water adjuvant can be AddaVax™.

To validate the FSBM recombinant protein according to the present invention can be used to immunize the animal subject to induce the production of the antibody against group C *streptococcus* and to protect the animal subject from death due to group C *streptococcus* infection, the following trials are carried out.

Trial (A).

In trial (A), the expression plasmid is transformed into the *E. coli* BL21(DE)pLysS cells. The FSBM recombinant protein is expressed by 0.5 mM IPTG and purified using $Ni^{2+}$ chelating chromatography. The purified FSBM recombinant protein is examined by SDS-PAGE. As shown in FIG. 1*a*, the FSBM recombinant protein (group A1) has a molecular weight of about 18 kDa.

Figure 1B:
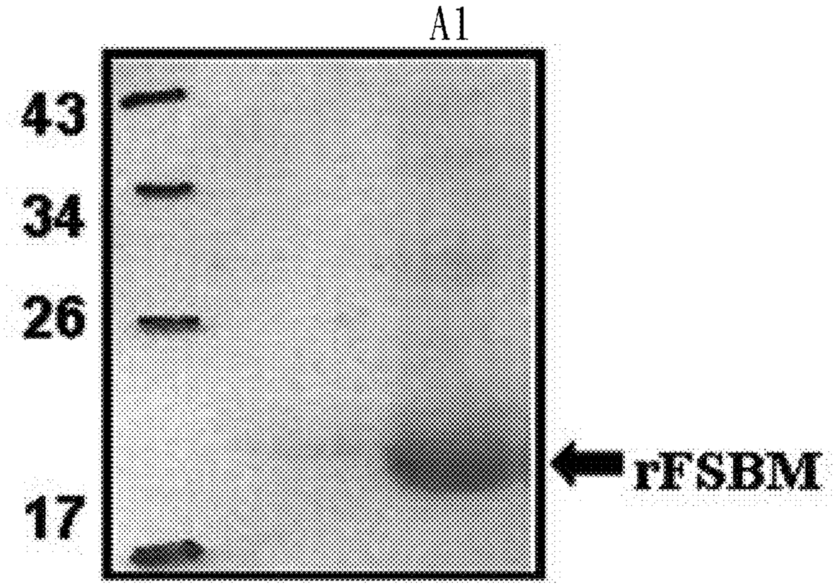
FIG. 1*b* depicts the Western blotting analysis of the FSBM recombinant protein according to the present invention by the anti-SPE B mouse serum.
Figure 1C:
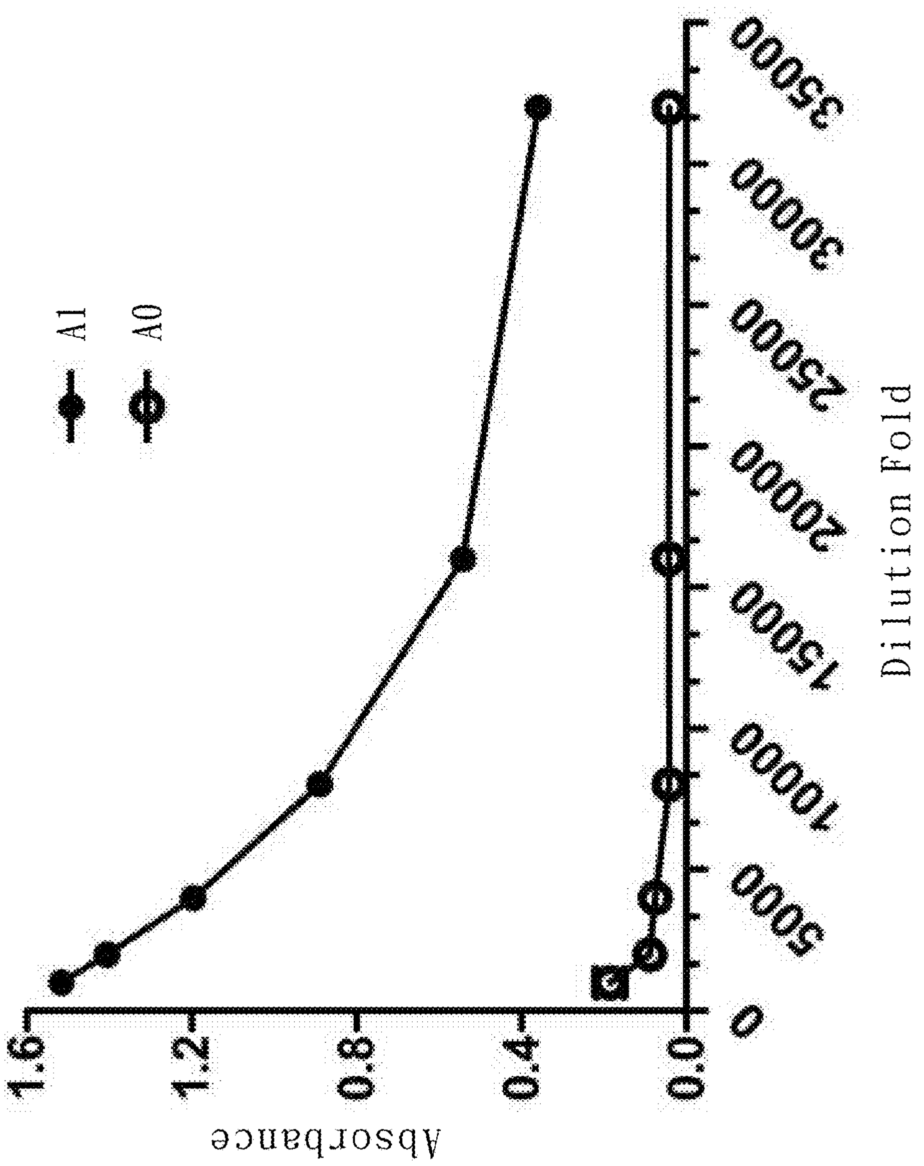
FIG. 1*c* depicts the ELISA analysis of the FSBM recombinant protein according to the present invention by the anti-SPE B mouse serum.

The purified FSBM recombinant protein is further analyzed by Western blotting and ELISA using the anti-SPE B mouse serum. As shown in FIGS. 1*b* and 1*c*, the FSBM recombinant protein (group A1) can be recognized by the anti-SPE B mouse serum.

Trial (B).

Figure 2:
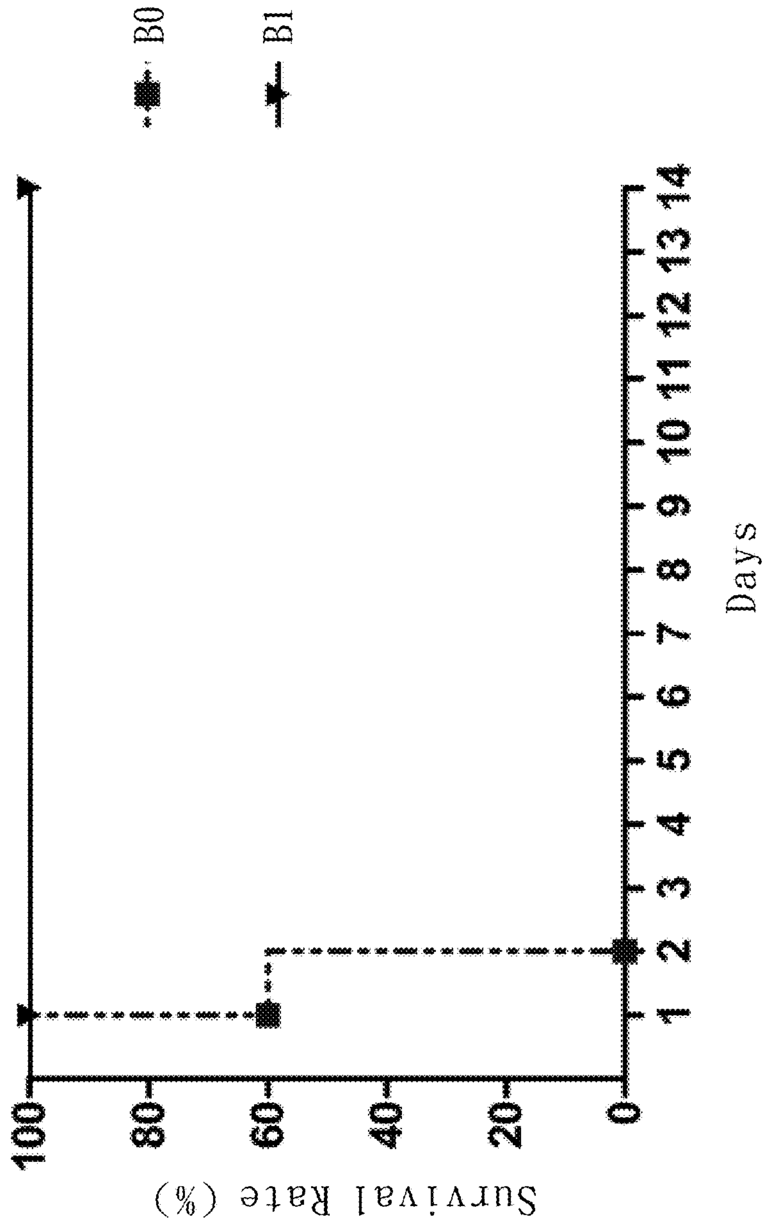
FIG. 2 depicts the survival rate analysis of the FSBM recombinant protein according to the present invention-immunized mice which are challenged with group C *streptococcus*.

In trial (B), the BALB/c mice are immunized with the FSBM recombinant protein (25 μg) combined with equal volume of the pharmaceutically-acceptable adjuvant by intraperitioneal injection (once in 7 days for 3 times). On day $28^{st}$ (7 days after the $3^{rd}$ immunization), the BALB/c mice are challenged with group C *streptococcus* ($9\times10^8$ CFU, ATCC 43078) by intraperitioneal injection. The survival rate of the BALB/c mice infected by group C *streptococcus* is recorded. As shown in FIG. 2, all of the BALB/c mice without immunizing with the FSBM recombinant protein (group B0) die on day $2^{nd}$, and all of the BALB/c mice with immunizing with the FSBM recombinant protein (group B1) survive until day $14^{th}$ (survival rate 100%). That is, the FSBM recombinant protein according to the present invention can effectively induce the production of the antibody against group C *streptococcus*, protecting the animal subjects from death due to group C *streptococcus* infection.

Trial (C).

Figure 3B:
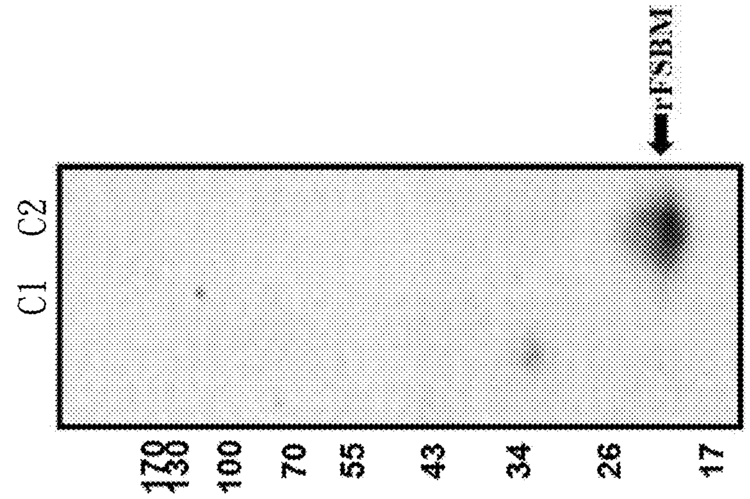
FIG. 3*b* depicts the Western blotting analysis of the porcine cardiac myosin by the FSBM recombinant protein-immunized serum.
Figure 3A:
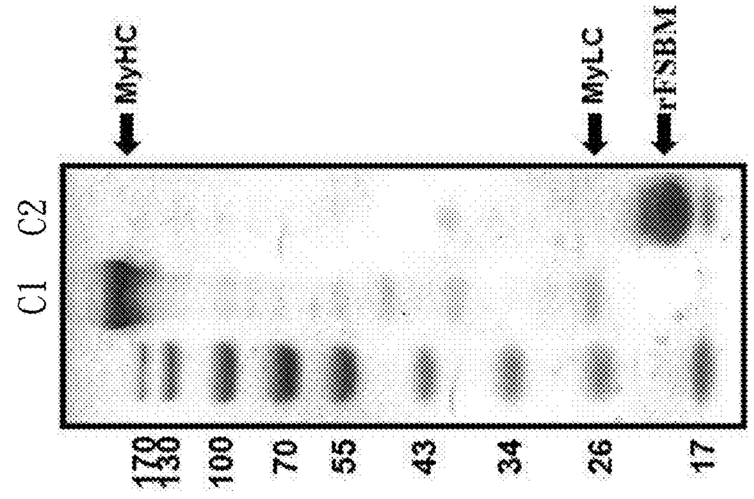
FIG. 3*a* depicts the SDS-PAGE analysis of the porcine cardiac myosin.

In trial (C), the serum collected from the BALB/c mice immunized with the FSBM recombinant protein are used. Referring to FIGS. 3*a* and 3*b*, the FSBM recombinant protein-immunized serum can recognize the FSBM recombinant protein (group C2), but not the porcine cardiac myosin (group C1), showing that immunization the animal subject with the FSBM recombinant protein according to the present invention will neither induce autoimmune response against cardiac tissues nor cause rheumatic heart disease.

Accordingly, immunizing the animal subject with the FSBM recombinant protein sufficiently facilitate production of antibody against group C *streptococcus* in the animal subject. With such performance, the animal subject shows a decreased risk of infection by group C *streptococcus*, as well as a reduced risk of dying due to group C *streptococcus* infection.

Although the invention has been described in detail with reference to its presently preferable embodiment, it will be understood by one of ordinary skill in the art that various modifications can be made without departing from the spirit and the scope of the invention, as set forth in the appended claims.

What is claimed is:

1. A FSBM recombinant protein for conferring protection against group C *streptococcus* infection in an animal subject, comprising:

a first peptide fragment, having the amino acid sequence set forth in SEQ ID NO. 5;

a second peptide fragment, having the amino acid sequence set forth in SEQ ID NO. 6;

a third peptide fragment, having the amino acid sequence set forth in SEQ ID NO. 7; and a fourth peptide fragment, having the amino acid sequence set forth in SEQ ID NO. 8.

2. The FSBM recombinant protein as claimed in claim 1, wherein the FSBM recombinant protein has the amino acid sequence set forth in SEQ ID NO. 10.

3. A method of protecting an animal subject against group C *streptococcus* infection by immunizing the animal subject with the FSBM recombinant protein as claimed in claim 1 to facilitate production of antibody against group C *streptococcus* in the animal subject.

4. The method as claimed in claim 3, wherein the FSBM recombinant protein is administered by intramuscular injection or subcutaneous injection.

5. The method as claimed in claim 4, wherein the FSBM recombinant protein is administered to the animal subject in a dosage of 1 mg/kg of the animal subject once in 7 days.

* * * * *

SEQUENCE LISTING

```
<160> NUMBER OF SEQ ID NOS: 10

<210> SEQ ID NO 1
<211> LENGTH: 114
<212> TYPE: DNA
<213> ORGANISM: Artificial Sequence
<220> FEATURE:
<223> OTHER INFORMATION: Nucleic acid sequence of the first DNA fragment
      being expressed as the peptide corresponding to the FnBR domain of
      Sfb1

<400> SEQUENCE: 1
```

-continued

```
agatctggta tgagtggaca aacaacacca caagtagaaa ctgaagacac caaggaaccc     60

ggggtgctga tgggcggcca gagcgagtct gttgaattca ctaaggatac ccag          114


<210> SEQ ID NO 2
<211> LENGTH: 63
<212> TYPE: DNA
<213> ORGANISM: Artificial Sequence
<220> FEATURE:
<223> OTHER INFORMATION: Nucleic acid sequence of the second DNA
      fragment being expressed as the peptide corresponding to the
      immunogenic domain of SLS

<400> SEQUENCE: 2

ttctcaattg ctaccgggtc tggaaattct caaggaggtt ctggatctta cacgccgggc     60

aag                                                                   63


<210> SEQ ID NO 3
<211> LENGTH: 69
<212> TYPE: DNA
<213> ORGANISM: Artificial Sequence
<220> FEATURE:
<223> OTHER INFORMATION: Nucleic acid sequence of the third DNA fragment
      being expressed as the peptide corresponding to the C3-binding
      motif of SPE B

<400> SEQUENCE: 3

gccctcggta caggcggtgg ggcaggaggg tttaacggct atcagtctgc cgtggtcgga     60

atcaagcct                                                             69


<210> SEQ ID NO 4
<211> LENGTH: 84
<212> TYPE: DNA
<213> ORGANISM: Artificial Sequence
<220> FEATURE:
<223> OTHER INFORMATION: Nucleic acid sequence of the fourth DNA
      fragment being expressed as the peptide corresponding to the
      C-terminal conserved segment of M protein

<400> SEQUENCE: 4

caggccgagg ataaagtgaa acaaagtagg gaggctaaga aacaggtgga gaaggcattg     60

aagcagcttg aggacaaagt ccag                                            84


<210> SEQ ID NO 5
<211> LENGTH: 38
<212> TYPE: PRT
<213> ORGANISM: Artificial Sequence
<220> FEATURE:
<223> OTHER INFORMATION: Amino acid sequence of the first peptide
      fragment corresponding to the FnBR domain of Sfb1

<400> SEQUENCE: 5

Arg Ser Gly Met Ser Gly Gln Thr Thr Pro Gln Val Glu Thr Glu Asp
1               5                   10                  15

Thr Lys Glu Pro Gly Val Leu Met Gly Gly Gln Ser Glu Ser Val Glu
            20                  25                  30

Phe Thr Lys Asp Thr Gln
        35


<210> SEQ ID NO 6
<211> LENGTH: 21
<212> TYPE: PRT
<213> ORGANISM: Artificial Sequence
<220> FEATURE:
<223> OTHER INFORMATION: Amino acid sequence of the second peptide
```

fragment corresponding to the immunogenic domain of SLS

<400> SEQUENCE: 6

```
Phe Ser Ile Ala Thr Gly Ser Gly Asn Ser Gln Gly Gly Ser Gly Ser
1               5                   10                  15

Tyr Thr Pro Gly Lys
            20
```

<210> SEQ ID NO 7
<211> LENGTH: 23
<212> TYPE: PRT
<213> ORGANISM: Artificial Sequence
<220> FEATURE:
<223> OTHER INFORMATION: Amino acid sequence of the third peptide fragment corresponding to the C3-binding motif of SPE B

<400> SEQUENCE: 7

```
Ala Leu Gly Thr Gly Gly Gly Ala Gly Gly Phe Asn Gly Tyr Gln Ser
1               5                   10                  15

Ala Val Val Gly Ile Lys Pro
            20
```

<210> SEQ ID NO 8
<211> LENGTH: 28
<212> TYPE: PRT
<213> ORGANISM: Artificial Sequence
<220> FEATURE:
<223> OTHER INFORMATION: Amino acid sequence of the fourth peptide fragment corresponding to the C-terminal conserved segment of M protein

<400> SEQUENCE: 8

```
Gln Ala Glu Asp Lys Val Lys Gln Ser Arg Glu Ala Lys Lys Gln Val
1               5                   10                  15

Glu Lys Ala Leu Lys Gln Leu Glu Asp Lys Val Gln
            20                  25
```

<210> SEQ ID NO 9
<211> LENGTH: 357
<212> TYPE: DNA
<213> ORGANISM: Artificial Sequence
<220> FEATURE:
<223> OTHER INFORMATION: Nucleic acid sequence used to express as the FSBM recombinant protein according to present invention

<400> SEQUENCE: 9

```
agatctggta tgagtggaca aacaacacca caagtagaaa ctgaagacac caaggaaccc     60

ggggtgctga tgggcggcca gagcgagtct gttgaattca ctaaggatac ccaggtcgac    120

ttctcaattg ctaccgggtc tggaaattct caaggaggtt ctggatctta cacgccgggc    180

aagtgcggta ccgccctcgg tacaggcggt ggggcaggag ggtttaacgg ctatcagtct    240

gccgtggtcg gaatcaagcc tggatcccag gccgaggata aagtgaaaca aagtagggag    300

gctaagaaac aggtggagaa ggcattgaag cagcttgagg acaaagtcca gtctaga       357
```

<210> SEQ ID NO 10
<211> LENGTH: 119
<212> TYPE: PRT
<213> ORGANISM: Artificial Sequence
<220> FEATURE:
<223> OTHER INFORMATION: Amino acid sequence of the FSBM recombinant protein according to the present invention

<400> SEQUENCE: 10

-continued

```
Arg Ser Gly Met Ser Gly Gln Thr Thr Pro Gln Val Glu Thr Glu Asp
1               5                   10                  15

Thr Lys Glu Pro Gly Val Leu Met Gly Gly Gln Ser Glu Ser Val Glu
            20                  25                  30

Phe Thr Lys Asp Thr Gln Val Asp Phe Ser Ile Ala Thr Gly Ser Gly
        35                  40                  45

Asn Ser Gln Gly Gly Ser Gly Ser Tyr Thr Pro Gly Lys Cys Gly Thr
    50                  55                  60

Ala Leu Gly Thr Gly Gly Gly Ala Gly Gly Phe Asn Gly Tyr Gln Ser
65                  70                  75                  80

Ala Val Val Gly Ile Lys Pro Gly Ser Gln Ala Glu Asp Lys Val Lys
                85                  90                  95

Gln Ser Arg Glu Ala Lys Lys Gln Val Glu Lys Ala Leu Lys Gln Leu
            100                 105                 110

Glu Asp Lys Val Gln Ser Arg
        115
```